United States Patent
Satyanarayana et al.

(10) Patent No.: US 7,858,793 B2
(45) Date of Patent: Dec. 28, 2010

(54) METHYL 2-[(3S)-[3-[2E)-(7-CHLORO QUINOLIN-2-YL) ETHENYL] PHENYL]-3-HALOPROPYL] BENZOATES

(76) Inventors: Chava Satyanarayana, Plot No.40, Park View Enclave, Manovikas Nagar, Hasmathpet Road, Secunderabad-500 009 (IN); Gorantla Seeta Ramanjaneyulu, Plot No-12, Sai Ansh Arcade Durgavihar Colony, Tirumalgherry, Secunderabad-500 015 (IN); Indukuri Venkata Sunil Kumar, Flat No-104, Raghavendra Tower, Kphb-Vi Phase, Kukatpally, Hyderabad-500 072 (IN); Simhadri Srinivas, Flat No-101, Shobana Tower, Vivekanandanagar Colony, Kukatpally, Hyderabad-500 072 (IN)

( * ) Notice: Subject to any disclaimer, the term of this patent is extended or adjusted under 35 U.S.C. 154(b) by 894 days.

(21) Appl. No.: 11/791,048

(22) PCT Filed: Jul. 19, 2004

(86) PCT No.: PCT/IN2004/000211

§ 371 (c)(1),
(2), (4) Date: May 17, 2007

(87) PCT Pub. No.: WO2006/008750

PCT Pub. Date: Jan. 26, 2006

(65) Prior Publication Data

US 2008/0275243 A1    Nov. 6, 2008

(51) Int. Cl.
*C07D 215/38*    (2006.01)

(52) U.S. Cl. .................... 546/159; 546/163

(58) Field of Classification Search ............... 546/159, 546/162

See application file for complete search history.

(56) References Cited

U.S. PATENT DOCUMENTS

| 5,565,473 A | 10/1996 | Belley et al. |
| 5,614,632 A | 3/1997 | Bhupathy et al. |
| 7,501,517 B2 * | 3/2009 | Overeem et al. ............ 546/174 |

FOREIGN PATENT DOCUMENTS

EP    0 480 717 B1    4/1992

OTHER PUBLICATIONS

Yoshida, Tetrahedron, vol. 55, pp. 2183-2192, 1999.*

* cited by examiner

*Primary Examiner*—D. Margaret Seaman
(74) *Attorney, Agent, or Firm*—Ladas & Parry LLP

(57) ABSTRACT

The present invention relates to the novel compounds Methyl 2-[(3S)-[3-[(2E)(7-chloro quinolin-2-yl)ethenyl]phenyl]-3-halopropyl]benzoates (IV) wherein the halo is chloro, bromo, iodo, starting from the known compound Methyl 2-[(3S)-[3-[(2E)-(7-chloroquinolin-2-yl)ethenyl]phenyl]-3-hydroxypropyl]benzoate (1). Reaction of Methyl 2-[(3S)-[3-[(2E)-(7-chloroquinolin-2-yl)ethenyl]phenyl]-3-hydroxypropyl] benzoate (1) with thionyl chloride or with methane sulfonyl chloride-lithium bromide or with trimethyl chlorosilane-sodium iodide in presence or absence of base gives Methyl 2-[(3S)-[3-[(2E)-(7-chloro quinolin-2-yl)ethenyl]phenyl]-3-halopropyl]benzoates.

11 Claims, No Drawings

METHYL 2-[(3S)-[3-[2E)-(7-CHLORO QUINOLIN-2-YL) ETHENYL] PHENYL]-3-HALOPROPYL] BENZOATES

The present invention relates to novel compounds that are useful intermediates in the preparation of Montelukast sodium and the process for their preparation.

Montelukast sodium namely Sodium 1-[[[(1R)-1-[3-[(1E)-2-(7-chloro-2-quinolinyl)ethenyl]phenyl]-3-[2-(1-hydroxy-1-methylethyl)phenyl]propyl]thio]methyl]cyclopropane acetic acid has the formula

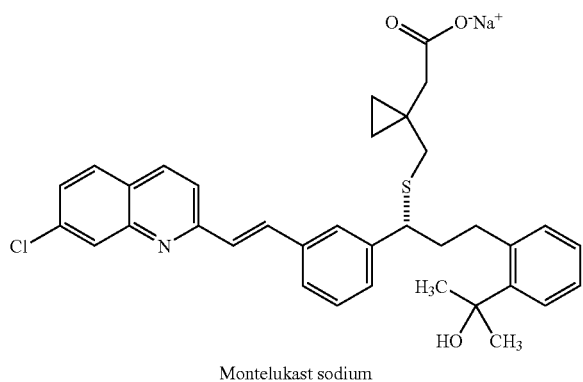

Montelukast sodium

Montelukast sodium is a leukotriene antagonist and inhibits the synthesis of leukotriene biosynthesis. It is useful as anti-asthamatic, anti-allergic, anti-inflammatory, cytoprotective agent and hence useful in the treatment of angina, cerebral spasm, glomerular nephratis, hepatic, endotoxemia, uveitis and allograft rejection.

European Patent No 480,717 discloses montelukast sodium along with other related compounds and the methods for their preparation. The reported method of syntheses proceeds through corresponding methyl ester namely, Methyl 2-[(3S)-[3-[(2E)-(7-chloroquinolin-2-yl)ethenyl]phenyl]-3-hydroxypropyl]benzoate (I) and involves coupling methyl 1-(mercaptomethyl)cyclopropaneacetate with a mesylate generated in-situ. The methyl ester of montelukast is hydrolyzed to free acids and the latter converted directly to montelukast sodium salt (Scheme-1). The process is not particularly suitable for large-scale production because it requires tedious chromatographic purification of the methyl ester intermediate and/or the final product and the product yield is low.

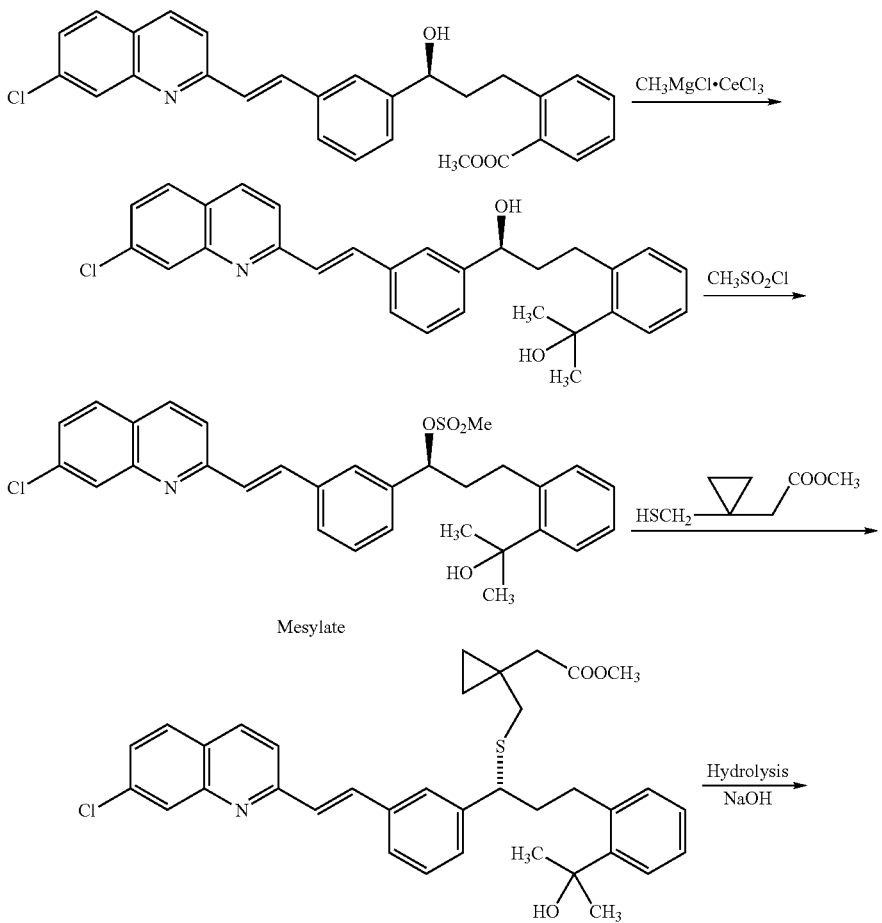

Scheme-1

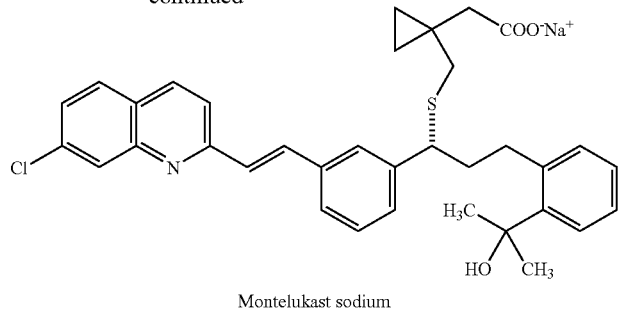

Montelukast sodium

U.S. Pat. No. 5,614,632 discloses an improved process for the preparation of crystalline montelukast sodium, which comprises of the following steps:

- Reaction of methyl 2-[3(S)-[3-[2-(7-chloroquinolin-2-yl) ethenyl]phenyl]-3-hydroxypropyl benzoate (Hydroxyester, I) with Grignard reagent, methyl magnesium chloride in presence of cerium chloride to give Diol (II)
- Reaction of Diol (II) with methane sulfonyl chloride to afford 2-[2-[3(s)-[3-(2-(7-chloro quinolin-2-yl)ethenyl] phenyl]-3-methane sulfonyloxy propyl]phenyl]-2-propanol (III)
- Condensation of 2-[2-[3(s)-[3-(2-(7-chloro quinolin-2-yl) ethenyl]phenyl]-3-methane sulfonyloxy propyl]phenyl]-2-propanol (III) with dilithium dianion of 1-(mercaptomethyl)cyclopropaneacetic acid, which has been generated by the reaction of 1-(mercaptomethyl)cyclopropaneacetic acid with n-Butyl lithium
- Isolation of the condensed product, montelukast as solid montelukast dicyclohexyl amine salt
- Purification and conversion of montelukast dicyclohexyl amine salt into montelukast sodium The reaction of Diol (II) with methane sulfonyl chloride involves the reaction temperature of about −25° C. and to store the intermediate, 2-[2-[3(s)-[3-(2-(7-chloro quinolin-2-yl)ethenyl]phenyl]-3-methane sulfonyloxypropyl]phenyl]-2-propanol (III) can be stored in a stable condition only under at low temperature below −15° C. for having the stability. The process further involves the formation of dilithium anion, which requires the usage of n-Butyl lithium under anhydrous conditions. n-Butyl lithium is also highly inflammable and hazardous reagent.

Scheme-2

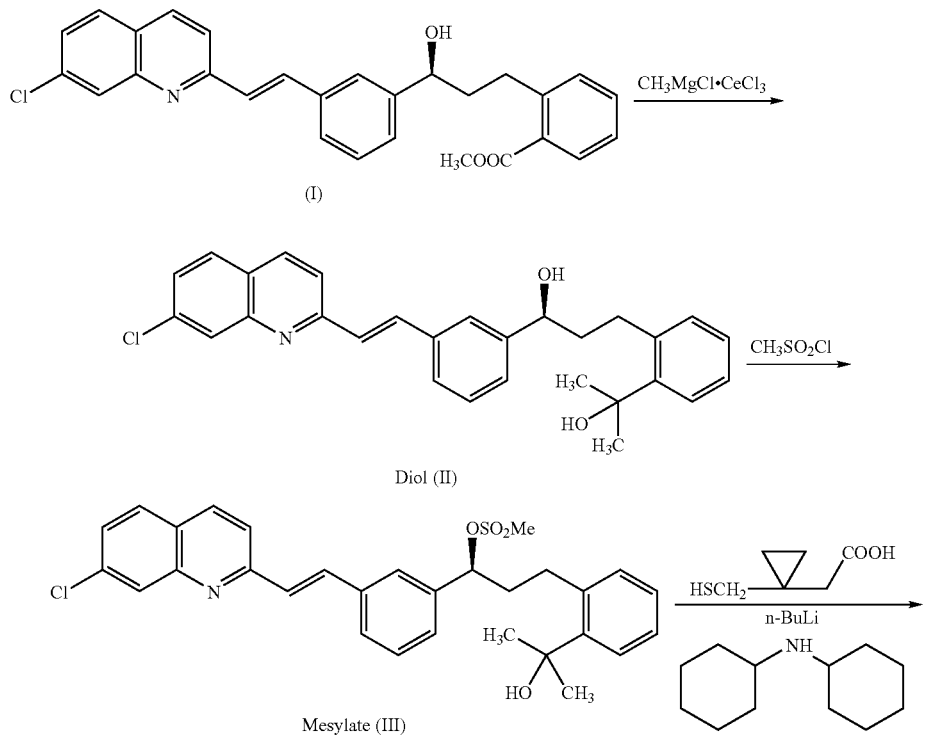

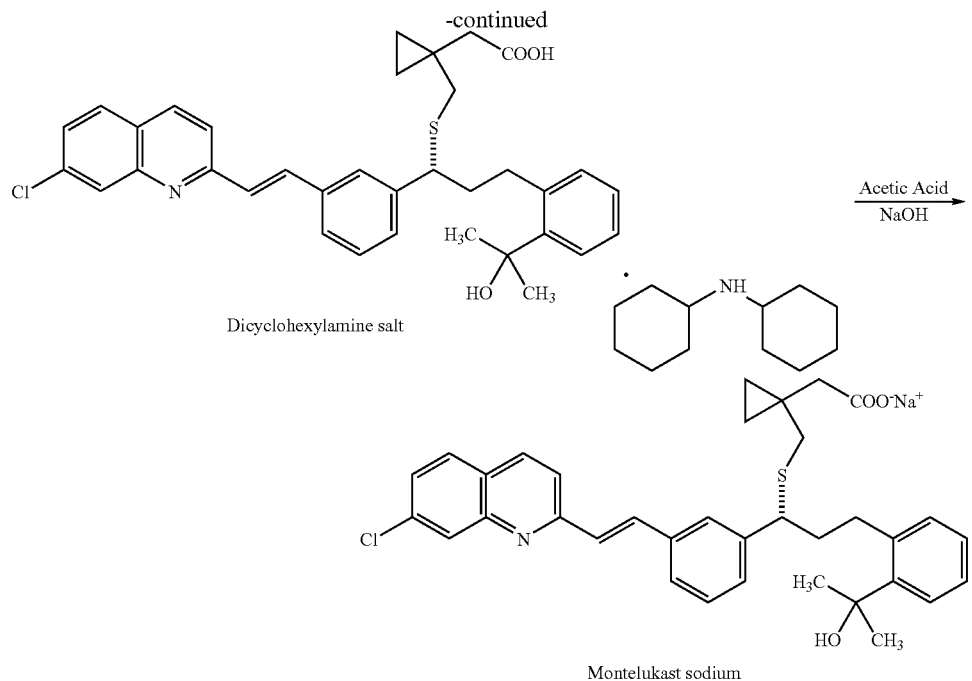

Dicyclohexylamine salt

Acetic Acid / NaOH →

Montelukast sodium

It is a long felt need of the industry to provide a process which avoids the usage of low temperature reactions viz. below −25° C., storage conditions of viz below −15° C., unstable intermediate (III), handling of highly inflammable and hazardous reagents for the preparation of montelukast sodium. This is ideally achieved through intermediates that are stable under normal condition.

The main object of the present invention is to provide novel compounds Methyl 2-[(3S)-[3-[(2E)-(7-chloro quinolin-2-yl)ethenyl]phenyl]-3-halopropyl]benzoates stable under normal conditions for use in the preparation of montelukast sodium thereby avoiding low temperature (below −25° C.) reactions, storage (−15° C.) conditions.

Another object of the invention is to provide a process for the preparation of Methyl 2-[(3S)-[3-[(2E)-(7-chloroquinolin-2-yl)ethenyl]phenyl]-3-halopropyl]benzoates.

Another object of the invention is to provide a process for the preparation of Methyl 2-[(3S)-[3-[(2E)-(7-chloroquinolin-2-yl)ethenyl]phenyl]-3-chloropropyl]benzoate for use in the preparation of montelukast sodium Another object of the invention is to provide a process for the preparation of Methyl 2-[(3S)-[3-[(2E)-(7-chloroquinolin-2-yl)ethenyl]phenyl]-3-bromopropyl]benzoate for use in the preparation of montelukast sodium Another object of the invention is to provide a process for the preparation of Methyl 2-[(3S)-[3-[(2E)-(7-chloroquinolin-2-yl)ethenyl]phenyl]-3-iodopropyl]benzoate for use in the preparation of montelukast sodium Yet another object of the invention is to provide fingerprinting of Methyl 2-[(3S)-[3-[(2E)-(7-chloro quinolin-2-yl)ethenyl]phenyl]-3-chloropropyl]benzoate using NMR, mass and IR spectral data.

Yet another object of the invention is to provide fingerprinting of Methyl 2-[(3S)-[3-[(2E)-(7-chloro quinolin-2-yl)ethenyl]phenyl]-3-bromopropyl]benzoate using NMR, mass and IR spectral data.

Yet another object of the invention is to provide fingerprinting of Methyl 2-[(3S)-[3-[(2E)-(7-chloro quinolin-2-yl)ethenyl]phenyl]-3-iodopropyl]benzoate using NMR, mass and IR spectral data Accordingly, the present invention relates to the novel compounds, process for the preparation of Methyl 2-[(3S)-[3-[(2E)-(7-chloro quinolin-2-yl)ethenyl]phenyl]-3-halopropyl]benzoates (IV) wherein the halo is chloro, bromo, iodo, starting from the known compound Methyl 2-[(3S)-[3-[(2E)-(7-chloroquinolin-2-yl)ethenyl]phenyl]-3-hydroxypropyl]benzoate (I). Reaction of Methyl 2-[(3S)-[3-[(2E)-(7-chloroquinolin-2-yl)ethenyl]phenyl]-3-hydroxypropyl]benzoate (I) with thionyl chloride or with methane sulfonyl chloride-lithium bromide or with trimethyl chlorosilane-sodium iodide in presence or absence of base gives Methyl 2-[(3S)-[3-[(2E)-(7-chloro quinolin-2-yl)ethenyl]phenyl]-3-halopropyl]benzoates (IV) wherein the halo is chloro, bromo, Iodo respectively (Scheme-3).

Scheme-3

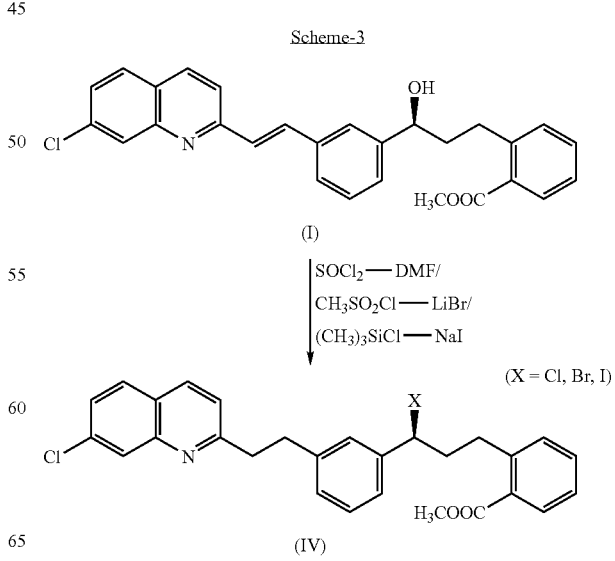

It may be noted that no hazardous reaction used or materials are used in the process of the present invention.

The present invention provides a process for the preparation of Methyl 2-[(3S)-[3-[(2E)-(7-chloro quinolin-2-yl)ethenyl]phenyl]-3-chloropropyl]benzoate comprising:
- Dehydration of Methyl 2-[(3S)-[3-[(2E)-(7-chloroquinolin-2-yl)ethenyl]phenyl-3-hydroxy propyl]benzoate
- Suspending anhydrous methyl 2-[(3S)-[3-[(2E)-(7-chloro quinolin-2-yl)ethenyl]phenyl]-3-hydroxy propyl]benzoate (I) in halogenated solvent
- Adding dimethyl formamide
- Cooling the reaction mass to low temperature
- Adding thionyl chloride at low temperature
- Raising the temperature and maintaining for about 1 hr to 6 hrs
- Removing the solvent
- Adding organic polar solvent
- Mixing the reaction mass
- Isolating and drying the product The present invention provides a process for the preparation of Methyl 2-[(3S)-[3-[(2E)-(7-chloro quinolin-2-yl)ethenyl]phenyl]-3-bromopropyl]benzoate comprising:
- Suspending anhydrous methyl 2-[(3S)-[3-[(2E)-(7-chloro quinolin-2-yl)ethenyl]phenyl]-3-hydroxy propyl]benzoate (I) in halogenated solvent
- Adding a base
- Cooling to low temperature
- Adding methane sulfonyl chloride at low temperature
- Maintaining at that low temperature
- Raising the temperature and maintaining for about 3 hrs to 8 hrs
- Quenching the reaction mass with water followed by separation of organic layer
- Washing the organic layer with water
- Drying the organic layer over dehydrating agents
- Removing the solvent
- Dissolving the residue in acetonitrile
- Adding Lithium bromide solution in acetonitrile
- Raising the temperature and maintaining the reaction mass
- Removing the solvent
- Adding DM water, water immiscible solvent
- Extracting the aqueous layer with water immiscible solvent
- Washing the organic layer with sodium bicarbonate, sodium chloride solution
- Removing the solvent
- Isolating Methyl 2-[(3S)-[3-[(2E)-(7-chloro quinolin-2-yl)ethenyl]phenyl]-3-bromopropyl]benzoate (IV, X=Br)

The present invention provides a process for the preparation of Methyl 2-[(3S)-[3-[(2E)-(7-chloro quinolin-2-yl)ethenyl]phenyl]-3-iodopropyl]benzoate comprising:
- Dissolving the anhydrous methyl 2-[(3S)-[3-[(2E)-(7-chloro quinolin-2-yl)ethenyl]phenyl]-3-hydroxy propyl]benzoate (I) in organic polar solvent
- Adding to a solution of sodium iodide
- Adding trimethyl chlorosilane to the reaction mass
- Raising the temperature and maintaining the reaction mass
- Isolating Methyl 2-[(3S)-[3-[(2E)-(7-chloro quinolin-2-yl)ethenyl]phenyl]-3-iodo propyl]benzoate (IV, X=I)
- Purifying the crude wet material if necessary The starting material methyl 2-[3(S)-[3-[2-(7-chloroquinolin-2-yl)ethenyl]phenyl]-3-hydroxypropyl benzoate (I) is prepared according to literature reported methods.

Dehydration of methyl 2-[3(S)-[3-[2-(7-chloroquinolin-2-yl)ethenyl]phenyl]-3-hydroxypropyl benzoate (I) is carried-out by azeotropic distillation with hydrocarbons such as toluene, benzene at reflux temperature of the solvent followed by cooling and removal of solvent under reduced pressure at temperature below about 60° C. till to get residue.

Suspending anhydrous methyl 2-[(3S)-[3-[(2E)-(7-chloro quinolin-2-yl)ethenyl]phenyl]-3-hydroxy propyl]benzoate (I) in halogenated solvent such as methylene chloride, ethylene dichloride, chloroform, preferable one is methylene chloride, addition of dimethyl formamide or triethyl amine, cooling the reaction mass to low temperature such as about −10° C. to about 25° C., preferably about 5° C. to about 15° C. and slow addition of thionyl chloride over a period of 10 min to 2 hrs at temperature of −10° C. to 25° C. preferably at about 5° C. to 15° C. Maintaining the reaction mass at temperature of about −10° C. to about 25° C. preferably at about 5° C. to 15° C. for about 15 min to about 4 hrs followed by raising the temperature to about 15° C. to about 35° C. preferably at about 20° C. to 25° C. and maintaining for about 1 hr to about 6 hrs. Removal of solvent under reduced pressure at temperature below 40° C. gives the chloro compound (IV, X=Cl) as residue.

The chloro compound is purified by suspending the residue in organic polar solvent such as acetonitrile, THF, removal of solvent under vacuum at temperature below 40° C., addition of fresh solvent, raising and maintaining the temperature of reaction mass at about 35° C. to 50° C. for about 10 min to about 2 hrs followed by cooling to about 15° C. to about 30° C., maintaining for about 10 min to 2 hrs, isolation and drying at temperature of about 40° C. to 60° C. gives the pure chloro derivative (IV, X=Cl).

Suspending anhydrous methyl 2-[(3S)-[3-[(2E)-(7-chloro quinolin-2-yl)ethenyl]phenyl]-3-hydroxy propyl]benzoate (I) in halogenated solvent such as methylene chloride, ethylene dichloride, chloroform, preferable one is methylene chloride, addition of base such as triethyl amine, diisopropyl ethyl amine, cooling the reaction mass to low temperature of about −15° C. to about 15° C., preferably about −10° C. to about 5° C. followed by slow addition of methane sulfonyl chloride over a period of 10 min to 2 hrs at temperature of −15° C. to 15° C. preferably at about −10° C. to 5° C. Maintaining the reaction mass at temperature of about −15° C. to about 15° C. preferably at about −10° C. to 5° C. for about 15 min to about 6 hrs followed by raising the temperature to about 15° C. to about 35° C. preferably at about 20° C. to 25° C. and maintaining for about 3 hrs to about 8 hrs. Quenching the reaction mass into water, settle, separating the layers followed by extraction of aqueous layer with halogenated solvent, washing the combined organic layer with water and removal of solvent under reduced pressure at temperature below 40° C. gives the residue.

Dissolving the residue in an organic polar solvent such as acetonitrile, THF, addition to lithium bromide solution in organic polar solvent such as acetonitrile, THF, at temperature of about 20° C. to about 40° C., raising the temperature to 50° C. to 90° C., maintaining for about 4 hrs to 12 hrs at temperature of 50° C. to 90° C., removal of solvent under reduced pressure gives the crude bromo derivative (IV, X=Br) as residue. The residue is purified by dissolving in water immiscible solvent such as methylene chloride, ethylene dichloride, washing the solution successively with water, sodium bicarbonate solution, sodium chloride solution, concentration of the organic layer and purification by flash chromatography gives the pure bromo derivative (IV, X=Br).

Adding anhydrous methyl 2-[(3S)-[3-[(2E)-(7-chloro quinolin-2-yl)ethenyl]phenyl]-3-hydroxypropyl]benzoate (1) solution in organic polar solvent such as acetonitrile, THF to a solution of sodium iodide at temperature of about 10° C. to about 25° C. followed by addition of trimethylchloro silane to the mass, raising the temperature to about 35° C. to about 55° C., maintaining the reaction mass at temperature of 35° C. to 55° C. for about 10 hrs to 24 hrs, isolation, slurring the wet cake with mixture of ethyl acetate, water gives the crude iodo derivative (IV, X=I). The crude on dissolution in mixture of methylene chloride, methanol followed by washing with sodium bicarbonate solution, water, drying over dehydrating agents such as anhydrous sodium sulphate, anhydrous magnesium sulphate, removal of solvent under reduced pressure at temperature below 50° C. followed by purification with column chromatography gives the pure methyl 2-[(3S)-[3-[(2E)-(7-chloro quinolin-2-yl)ethenyl]phenyl]-3-iodopropyl]benzoate (IV, X=I).

The NMR, IR and elemental analysis indicate that these compounds are novel and not reported in literature till date.

The Methyl 2-[(3S)-[3-[(2E)-(7-chloro quinolin-2-yl)ethenyl]phenyl]-3-halopropyl]benzoate compounds after isolation and purification and/or in situ without isolation may be used for the preparation of montelukast sodium.

The invention is now illustrated with a few non-limiting examples.

EXAMPLE-I

Preparation of Methyl 2-[(3S)-[3-[(2E)-(7-chloro quinolin-2-yl)ethenyl]phenyl]-3-chloropropyl]benzoate (IV, X=Cl)

Step-1: 100 g Methyl-2-[3(S)-[3-[2-(7-chloroquinolin-2-yl)ethenyl]phenyl]-3-hydroxy propyl benzoate is suspended in toluene (1000 ml) and temperature is raised and maintained at 8° C. for about 15 min. Insolubles are filtered, the clear solution is dehydrated by azeotropic distillation at temperature 108° C. to 112° C. The reaction mass is cooled to 60° C. and distilled off toluene under reduced pressure at temperature below 60° C. to get the residue.

Step-2: The above obtained residue is dissolved in Methylene chloride (1500 ml) at 25-35° C. DMF (50 ml) is added to the solution and cooled the reaction mass to 10° C. Thionyl chloride (78 g) is slowly added at 8° C. to 12° C. over 40 min, mixed for about 15 min, the temperature of the reaction mass is raised and maintained at 20° C. to 25° C. for 2 hrs. Reaction mass is concentrated under vacuum at temperature below 35° C. Acetonitrile (100 ml) is added to the reaction mass and distilled off acetonitrile under vacuum at temperature below 40° C. Fresh Acetonitrile (500 ml) is added to the mass, raised the temperature and maintained at 40° C. to 45° C. for 30 min. Reaction mass is cooled and maintained at 25° C. to 30° C. for 30 min. Product is filtered, washed the wet cake with acetonitrile (50 ml) and dried at 45° C. to 50° C. till constant weight.

Dry wt of the chloro ester is 70 g (yield is 69.9%)

Elemental analysis: C: 70.29%, H: 4.78%, N, 3.0% and calculated values for $C_{28}H_{23}Cl_2NO_2$ C: 70.59%, H, 4.83%, N: 2.94%

IR Spectrum (KBr, cm$^{-1}$): 3057, 2949, 2926, 2854, 1717, 1637, 1607, 1596, 1551, 1497, 1434, 1262, 1188, 1164, 1130, 1082, 1069, 966, 938, 929, 865, 838, 755, 710, 696

$^1$H NMR (300 MHz, CDCl$_3$, ppm): 8.09 (m, 2H), 7.92 (d, 1H), 7.68 (m, 4H), 7.25-7.55 (m, 8H), 4.94 (dd, 1H), 3.86 (s, 3H), 2.99-3.28 (m, 2H), 2.3-2.52 (m, 2H).

Mass Spectrum (M+): 476.1

EXAMPLE-II

Preparation of Methyl 2-[(3S)-[3-[(2E)-(7-chloro quinolin-2-yl)ethenyl]phenyl]-3-bromopropyl]benzoate (IV, X=Br)

Step-1 is followed the same procedure as given in example-I.

Step-2: Residue obtained in Step-1 is dissolved in methylene chloride (1000 ml) at 25° C. to 35° C., to that triethylamine (92 ml) is added and the reaction mass is cooled to −5° C. Methane sulfonyl chloride (33 ml) is added at −5° C. to −3° C. over 60 min and the reaction mass is maintained at −5° C. to −2° C. for 2 hrs. Reaction mass temperature is raised and maintained at 20° C. to 25° C. for 5 hrs. Reaction mass is quenched into chilled water (200 ml), allowed to settle, layers are separated; Aqueous layer is extracted with methylene chloride (2×300 ml). Combined organic layer is dried over anhydrous sodium sulphate (15 g) and distilled off the methylene chloride under vacuum. Residue is dissolved in acetonitrile (200 ml) and added to lithium bromide solution (38 g in 600 ml acetonitrile). Reaction mass temperature is raised and maintained at reflux temperature for about 6 hrs. Acetonitrile is distilled under vacuum at temperature below 45° C. and methylene chloride (1000 ml) and water (1000 ml) are added to the mass. Reaction mass is mixed for 15 min, allowed to settle, separated the layers, extracted the aqueous layer with methylene chloride (300 ml). Combined organic layer is washed with 5% sodium bicarbonate solution (400 ml) followed by DM water (2×300 ml) and methylene chloride is distilled completely. Finally the residue is purified by flash chromatography using chloroform:methanol (95:5).

Wt of the bromo derivative is 42 g (yield 36.9%)

Elemental analysis: C, 65.00%, H, 4.58%, N, 2.70% and calculated values for $C_{28}H_{23}BrClNO_2$ C: 64.57%, H, 4.45%, N, 2.69%

IR Spectrum (KBr, cm$^{-1}$): 3423, 3025, 2949, 1939, 1721, 1607, 1551, 1497, 1434, 1410, 1292, 1262, 1189, 1165, 1131, 1081, 965, 938, 929, 865, 838, 800, 754, 710, 692, 666, 621 and 589

$^{13}$C NMR (300 MHz, CDCl$_3$, ppm): 37.58, 41.3, 51.96, 63.16, 119.49, 125.57, 126.03, 126.58, 126.97, 128.10, 128.48, 128.59, 128.86, 129.56, 129.92, 130.46, 130.67, 130.99, 132.15, 135.0, 135.41, 136.0, 136.39, 138.03, 141.57, 148.56, 156.7, 167.7

Mass Spectrum (M+): 522

EXAMPLE-III

Preparation of Methyl 2-[(3S)-[3-[(2E)-(7-chloro quinolin-2-yl)ethenyl]phenyl]-3-iodopropyl]benzoate (IV, X=I)

Step-1 is followed the similar procedure as given in example-I.

Step-2: The residue obtained in step-1 is dissolved in acetonitrile (600 ml) at 25-35° C. and the mass is added to a solution of sodium iodide (98 g) in acetonitrile (600 ml) at temperature 15° C. to 20° C. over 10 min. Trimethylchloro silane (70.2 g) is added slowly to the reaction mass at 15° C. to 20° C. over 15 min. Temperature of the reaction mass is raised and maintained at 40° C. to 45° C. for 15 hrs. The product is filtered, washed with mixture of 1:1 ethyl acetate (500 ml) and water (500 ml). Wet cake is dissolved in a mixture of methylene chloride (1300 ml) and methanol (65 ml) at temperature 25° C. to 30° C. by mixing for about 30 min. Washed the solution with 5% sodium bicarbonate (325 ml) followed by DM water (2×325 ml) and separated the layers. Organic layer is dried over anhydrous sodium sulphate (15 g), distilled off the solvent at temperature below 40° C. Finally the residue is purified by flash chromatography using chloroform:methanol (95:5)

Weight of iodo derivative is 45 g (yield 34.9%)

Elemental analysis: C, 59.02%, H, 4.12%, N, 2.42% and calculated values for $C_{28}H_{23}ClINO_2$ C: 59.20%, H, 4.05%, N: 2.47%

IR Spectrum (KBr, $cm^{-1}$): 3022, 2948, 1717, 1635, 1607, 1497, 1433, 1410, 1293, 1260, 1188, 1163, 1132, 1078, 965, 929, 865, 838, 754, 709, 695, 667 and 622

$^1$H NMR (300 MHz, $CDCl_3$, ppm): 8.07-8.12 (m, 2H), 7.90-7.93 (m, 1H), 7.63-7.73 (m, 5H), 7.26-7.52 (m, 7H), 5.20 (t, 1H), 3.88 (s, 3H), 3.10-3.19 (m, 1H), 2.93-3.02 (m, 1H), 2.65-2.72 (m, 1H), 2.43-2.50 (m, 1H).

Mass Spectrum (M+): 568

We claim:

1. A process for the preparation of methyl-2-[(3S)-[3-[(2E)-(7-chloro quinolin-2-yl)ethenyl]phenyl]-3-chloropropyl]benzoates comprising:
    suspending methyl 2-[(3S)-3-[(2E)-(7-chloroquinolin-2-yl)ethenyl]phenyl-3-hydroxy propyl]benzoate in a halogenated solvent and adding a base,
    cooling the mass to a low temperature and adding thionyl chloride at low temperature,
    raising the temperature and maintaining the temperature for about 1 hr to 6 hrs,
    removing the solvent and adding a polar organic solvent, and
    isolating and drying the product.

2. A process as claimed in claim 1, wherein the halogenated solvent is methylene chloride, ethylene dichloride, chloroform or a mixture thereof, more preferably methylene chloride.

3. A process as claimed in claim 1, wherein the base is selected from DMF and triethylamine.

4. A process as claimed in claim 1, wherein the organic polar solvent is selected from acetonitrile and tetrahydrofuran.

5. A process for the preparation of methyl 2-[(3S)-[3-[(2E)-(7-chloro quinolin-2-yl)ethenyl]phenyl]-3-bromopropyl]benzoate comprising
    suspending methyl 2-[(3S)-3-[(2E)-(7-chloro quinolin-2-yl)ethenyl]phenyl]-3-hydroxy propyl]benzoate (I) in a halogenated solvent and adding a base,
    cooling the reaction mixture to a low temperature and adding methane sulfonyl chloride at low temperature,
    raising the temperature and maintaining the temperature for about 3 hrs to 8 hrs,
    quenching the reaction mass into water followed by isolating the organic layer,
    washing the organic layer with water and drying the organic layer over dehydrating agents,
    removing the solvent and dissolving the residue in acetonitrile,
    adding the solution to a lithium bromide solution in acetonitrile,
    raising the temperature to 50° C. to 90° C. and maintaining the temperature for about 4 hrs to 12 hrs,
    removing the solvent, adding DM water and a water immiscible solvent,
    separating the layers and extracting the aqueous layer with a water immiscible solvent,
    washing the organic layer with a sodium bicarbonate and a sodium chloride solution, and
    removing the solvent and isolating the product.

6. A process as claimed in claim 5, wherein the halogenated solvent is methylene chloride, ethylene dichloride, chloroform or a mixture thereof, more preferably methylene chloride.

7. A process as claimed in claim 5, wherein the base is triethyl amine or diisopropyl ethylamine.

8. A process claimed in claim 5, wherein the water immiscible solvent is methylene chloride or ethylene chloride.

9. A process for the preparation of methyl-2-[(3S)-[3-[(2E)-(7-chloro quinolin-2-yl)ethenyl]phenyl]-3-iodopropyl]benzoate comprising:
    dissolving the anhydrous methyl 2-[(3S)-[3-[(2E)-(7-chloro quinolin-2-yl)ethenyl]phenyl]-3-hydroxy propyl]benzoate (I) in an organic polar solvent,
    adding the solution to a solution of sodium iodide followed by trimethyl chlorosilane,
    raising the temperature and maintaining the reaction mass, and
    isolating the product and purifying the crude wet product if necessary.

10. A process as claimed in claim 9, wherein the organic polar solvent is acetonitrile or tetrahydrofuran.

11. A process for the preparation of Montelukast, which comprises utilizing methyl-2-[(3S)-[3-[(2E)-(7-chloro quinolin-2-yl)ethenyl]phenyl]-3-halopropyl]benzoate.

* * * * *